US009618507B2

(12) United States Patent
Kass

(10) Patent No.: US 9,618,507 B2
(45) Date of Patent: Apr. 11, 2017

(54) METHODS OF TREATING RHEUMATOID ARTHRITIS

(71) Applicant: Betanien Hospital, Skien (NO)

(72) Inventor: Anita Kass, Porsgrunn (NO)

(73) Assignee: BETANIEN HOSPITAL, Skien (NO)

( * ) Notice: Subject to any disclaimer, the term of this patent is extended or adjusted under 35 U.S.C. 154(b) by 0 days.

(21) Appl. No.: 14/628,529

(22) Filed: Feb. 23, 2015

(65) Prior Publication Data

US 2015/0238559 A1 Aug. 27, 2015

Related U.S. Application Data

(60) Provisional application No. 61/943,787, filed on Feb. 24, 2014.

(51) Int. Cl.
*A61K 38/08* (2006.01)
*G01N 33/564* (2006.01)
*A61K 38/09* (2006.01)

(52) U.S. Cl.
CPC .......... *G01N 33/564* (2013.01); *A61K 38/09* (2013.01); *G01N 2800/102* (2013.01)

(58) Field of Classification Search
None
See application file for complete search history.

(56) References Cited

U.S. PATENT DOCUMENTS

| 7,569,688 B2 | 8/2009 | Hirano et al. |
| 8,076,367 B2 | 12/2011 | Hirano et al. |
| 2004/0138138 A1 | 7/2004 | Engel et al. |

FOREIGN PATENT DOCUMENTS

| EP | 2505204 | 10/2012 |
| WO | 2009/106597 | 9/2009 |
| WO | 2011/144756 | 11/2011 |
| WO | 2014/104791 | 7/2014 |

OTHER PUBLICATIONS

Kass et al. ("Short-term treatment with a gonadotropin-releasing hormone antagonist, cetrorelix, in rheumatoid arthritis (AGRA): a randomized, double blind, placebo controlled study" Scand J Rheumatol, 2014; 43:22-27, epub Nov. 1, 2013).*
Kuiper et al. ("Influence of Sex, Age and Menopausal State on the Course of Early Rheumatoid Arthritis", The Journal of Rheumatology 2001: 28:8).*
Kass et al. (Cetrorelix, a Gonadotropin-releasing hormone, reduces disease activity and tumor necrosis factor-alpha in rheumatoid arthritis: A proof of concept, double blind, parallel group randomized controlled trial (AGRA Trial) ; The Endocrine Society's 94th Annual Meeting and Expo, presented Jun. 23, 2012).*
Anonymous: "Sifasi-HP", Feb. 1, 2001, Retrieved from the Internet: URL: http://www.seruminstitute.com/content/products/pdf/setrosil.pdf.
Ansari MA, et al., "Modulation of diabetes with gonadotropin-releasing hormone antagonists in the nonobese mouse model of autoimmune diabetes." Endocrinology 2004;145:337-42.
Azad N, et al., "Immunoactivation enhances the concentration of luteinizing hormone-releasing hormone peptide and its gene expression in human peripheral T-lymphocytes." Endocrinology 1993;133:215-23.
Chen A, et al., "The neuropeptides GnRH-II and GnRH-I are produced by human T cells and trigger laminin receptor gene expression, adhesion, chemotaxis and homing to specific organs." Nat Med 2002;8:1421-6.
Gordon D, et al., "Prolonged hypogonadism in male patients with rheumatoid arthritis during flares in disease activity." Br J Rheumatol 1988;27:440-44.
International Search Report, International Patent Application No. PCT/EP2015/069369, mailed Feb. 19, 2016.
Iqbal J, et al., "Follicle-stimulating hormone stimulates TNF production from immune cells to enhance osteoblast and osteoclast formation." Proc Natl Acad Sci USA 2006;103:14925-30.
Jacobson JD, et al., "Gonadotropin-releasing hormone increases CD4 T-lymphocyte numbers in an animal model of Immunodeficiency" J Allergy Clin Immunol 1999;104:653-58.
Kass et al., "The association of luteinizing hormone and follicle-stimulating hormone with cytokines and markers of disease activity in rheumatoid arthritis: a case-control study" Scand J Rheumatol 2010;39:109-17.
Kass et al. "Cetrorelix, a Gonadotropin-Releasing Hormone Antagonist, Demonstrates Efficacy and Significantly Reduces Proinflammatory Cytokines in Patients with Active Longstanding Rheumatoid Arthritis with High Gonadotropin Levels: A Proof-of-Concept, Double-Blind, Randomized Trial", 77th Annual Meeting of the American-College-of-Rheumatology (ACR) / 48th Annual Meeting of the Association, Dec. 1, 2013, pp. 1-3.
Kass et al. "Cetrorelix, a Gonadotropin-Releasing Hormone Antagonist, Significantly Reduces Tumour-necrosis-Factor-Alpha and Demonstrates Efficacy in Patients with Active Rheumatoid Arthritis: A Proof-of-Concept, Double-Blind, Randomised Trial", Arthritis & Rheumatism, vol. 64, No. 10, Suppl. S, Oct. 1, 2012, pp. S363-S364.
Kjeldsen-Kragh et al., "Controlled trial of fasting and one-year vegetarian diet in rheumatoid arthritis." Lancet 1991;338:899-902.
Morale MC, et al., "Blockade of central and peripheral luteinizing hormone-releasing hormone (LHRH) receptors in neonatal rats with a potent LHRH-antagonist inhibits the morphofunctional development of the thymus and maturation of the cell-mediated and humoral immune responses." Endocrinology 1991;128:1073-85.
Ostensen M, et al., "Effect of Pregnancy and Hormonal Changes on the Activity of Rheumatoid Arthritis" Scand J Rheumatol 1983;12:69-72.
Peter et al. "781 Androgen Deprivation Therapy by a Gonadotropin Releasing Hormone Antagonist, Degarelix, Lowers the Risk of Cardiovascular Events or Death when Compared to Luteinising Hormone-Releasing Agonists", Journal of Urology, vol. 189, No. 4, May 6, 2013.

(Continued)

*Primary Examiner* — James H Alstrum Acevedo
*Assistant Examiner* — Tara Martinez
(74) *Attorney, Agent, or Firm* — Casimir Jones S.C.

(57) ABSTRACT

The present invention relates to methods for the treatment of rheumatoid arthritis. In particular, the present invention relates to methods of treating rheumatoid arthritis with GnRH antagonists in patients with high gonadotropin and/or GnRH levels.

7 Claims, 11 Drawing Sheets

(56) References Cited

OTHER PUBLICATIONS

Pikwer et al., "Early menopause is an independent predictor of rheumatoid arthritis" Ann Rheum Dis 2012;71:378-81.
Rick FG, et al., "LHRH antagonist Cetrorelix reduces prostate size and gene expression of proinflammatory cytokines and growth factors in a rat model of benign prostatic hyperplasia." Prostate 2011;71:736-47.
Sabharwal P, et al., "Human thymocytes secrete luteinizing hormone: an autocrine regulator of T-cell proliferation." Biochem Biophys Res Commun 1992;187:1187-92.
Smith et al. "Gonadotropin-Releasing Hormone Blockers and Cardiovascular Disease Risk: Analysis of Prospective clinical Trials of Degarelix", Journal of Urology, vol. 186, No. 5, Nov. 1, 2011, pp. 1835-1842.
Tan AL, et al., "Role of oestrogen in the development of joint symptoms?" Lancet Oncology 2008;9:817-18.
Wen J, et al., "Luteinizing Hormone-Releasing Hormone (LHRH)-I antagonist cetrorelix inhibits myeloma cell growth in vitro and in vivo." Mol Cancer Ther 2011;10:148-58.
Wilhelmina CM et al. "MP24-11 GNRH Antagonists Associate with less weight gain and milder characteristics of the metabolic syndrome and atherosclerosis compared to surgical castration and GNRH analogues in pre-clincical animal model", Journal of Urology, vol. 191, No. 4, May 18, 2014.
Yanagita et al. "Astellas' Drug Discovery Strategy: Focus on Oncology", Japanese Journal of Clinical Oncology, vol. 42, No. 4, Mar. 28, 2012, pp. 241-246.

* cited by examiner

METHODS OF TREATING RHEUMATOID ARTHRITIS

FIELD OF THE INVENTION

The present invention relates to methods for the treatment of rheumatoid arthritis. In particular, the present invention relates to methods of treating rheumatoid arthritis with gonadotropin-releasing hormone (GnRH) antagonists in patients with high gonadotropin and/or GnRH levels.

BACKGROUND OF THE INVENTION

Rheumatoid arthritis (RA) is a chronic, systemic inflammatory disorder that may affect many tissues and organs, but principally attacks the joints producing an inflammatory synovitis that progresses to cartilage and bone destruction. Rheumatoid arthritis can also produce diffuse inflammation in the lungs, pericardium, pleura, and sclera, and also nodular lesions, most common in subcutaneous tissue under the skin. Although the cause of rheumatoid arthritis is unknown, autoimmunity plays a role in its chronicity and progression.

About 1% of the world's population is afflicted by rheumatoid arthritis, women three times more often than men. Onset is most frequent between the ages of 40 and 50, but people of any age can be affected. It can be a disabling and painful condition, which can lead to substantial loss of functioning and mobility. It is diagnosed chiefly on symptoms and signs, but also with blood tests (e.g., a test for CCP antibodies) and X-rays. Diagnosis and long-term management are typically performed by a rheumatologist, an expert in the diseases of joints and connective tissues (see, e.g., Majithia V, and Geraci S A (2007) Am. J. Med. 120 (11): 936-9; herein incorporated by reference in its entirety).

Current treatments for rheumatoid arthritis include: non-steroidal anti-inflammatory drugs (NSAIDs), corticosteroids, gold therapy, methotrexate, tumor necrosis factor Inhibitors such as etanercept (Enbrel®), adalimumab (Humira®), and infliximab (Remicade®), and other immunomodulatory and cytotoxic agents. While these treatments can be effective many require close supervision because of hazardous side effects. Response to treatment with these agents is variable and some patients still experience pain and joint degeneration. Thus, there is a need for additional treatments for rheumatoid arthritis and related diseases.

SUMMARY OF THE INVENTION

The present invention relates to methods for the treatment of rheumatoid arthritis. In particular, the present invention relates to methods of treating rheumatoid arthritis with GnRH antagonists in patients with high gonadotropin and/or GnRH levels.

Embodiments of the present invention provide methods and uses of treating rheumatoid arthritis, comprising: a) identifying subjects that have increased levels of GnRH or gonadotropins relative to a reference level; and b) administering a GnRH antagonist to the subjects. In some embodiments, increased levels of GnRH or gonadotropins are luteinizing hormone (LH) and/or follicle-stimulating hormone (FSH) levels above a reference level (e.g., approximately LH>15 IU/o (e.g., greater than 17.3 IU/L) and/or FSH>16.7 IU/L (e.g., greater than 34.6 IU/L)). In some embodiments, subjects to be treated do not have levels of GnRH or gonadotropins below the threshold level (e.g., as defined herein). In some embodiments, the reference level is adjusted based on age, gender, and menopausal status. For example, in some embodiments, males have LH levels greater than 3 and/or FSH levels greater than 5. In some embodiments, premenopausal women have LH>5 and/or FSH>8 or are in the early to late follicular phase of the menstrual cycle. In some embodiments, postmenopausal women have LH>15 and/or FSH>16.7. The present invention is not limited to a particular GnRH antagonist. In some embodiments, GnRH antagonists are small molecules or peptides (e.g., peptides comprising one or more synthetic amino acids), or peptide mimetics. Examples include, but are not limited to, cetrorelix, ganirelix, abarelix, degarelix, detirelix, iturelix, ozarelix, prazarelix, elagolix, ramorelix, or teverelix. In some embodiments, the identifying comprises performing a quantitative diagnostic assay. In some embodiments, the subject is a woman (e.g., a post-menopausal woman). In some embodiments, the subject is a woman over 40 or a male over 70. In some embodiments, the GnRH antagonist is administered in combination with an additional treatment for rheumatoid arthritis.

The present invention further provides the use of a GnRH antagonist in the treatment of rheumatoid arthritis in a subject that has increased levels of GnRH or gonadotropins relative to a reference level.

Further embodiments of the present invention provide methods and uses of treating rheumatoid arthritis, comprising: a) identifying subjects that exhibit one or more of: are negative for anti-cyclic citrullinated peptide (CCP) antibodies; are non-responders to anti-TNF therapy or disease-modifying anti-rheumatic drugs (DMARDs); or are not taking concomitant therapy; and b) administering a GnRH or gonadotropin antagonist to the subjects.

Additional embodiments will be apparent to persons skilled in the relevant art based on the teachings contained herein.

DEFINITIONS

Figure 1:
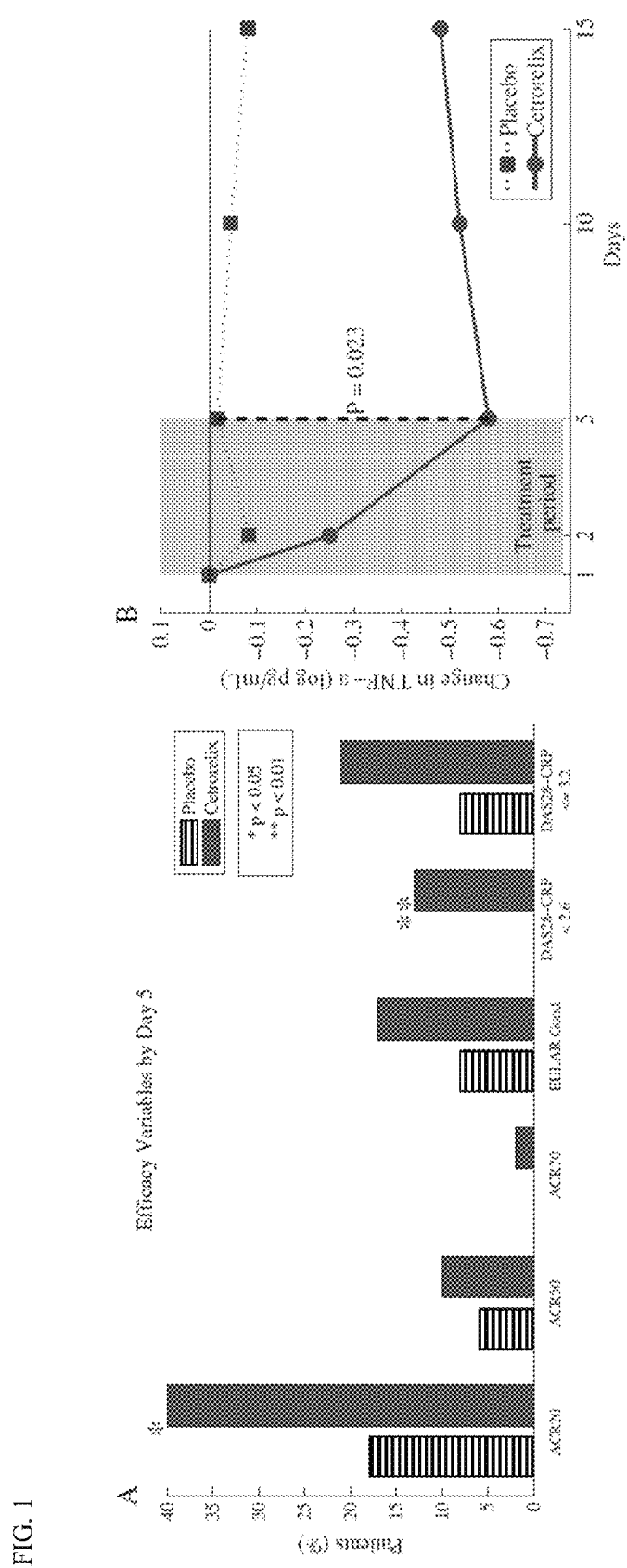
FIG. 1. (A) Efficacy variables by day 5. Change from baseline in the cetrorelix and placebo groups for (B) Tumour Necrosis Factor-α (TNF-α), (C) Luteinizing Hormone (LH) and (D) C-reactive protein (CRP). (E) Scatterplot of relative change of LH and TNF-α from baseline to day 5 in the cetrorelix and placebo groups. On both axes, 1.0 denotes no change. On the left side of the vertical line are patients whose levels of TNF-α decreased, and on the right side are patients whose levels of TNF-α increased.
Figure 1:
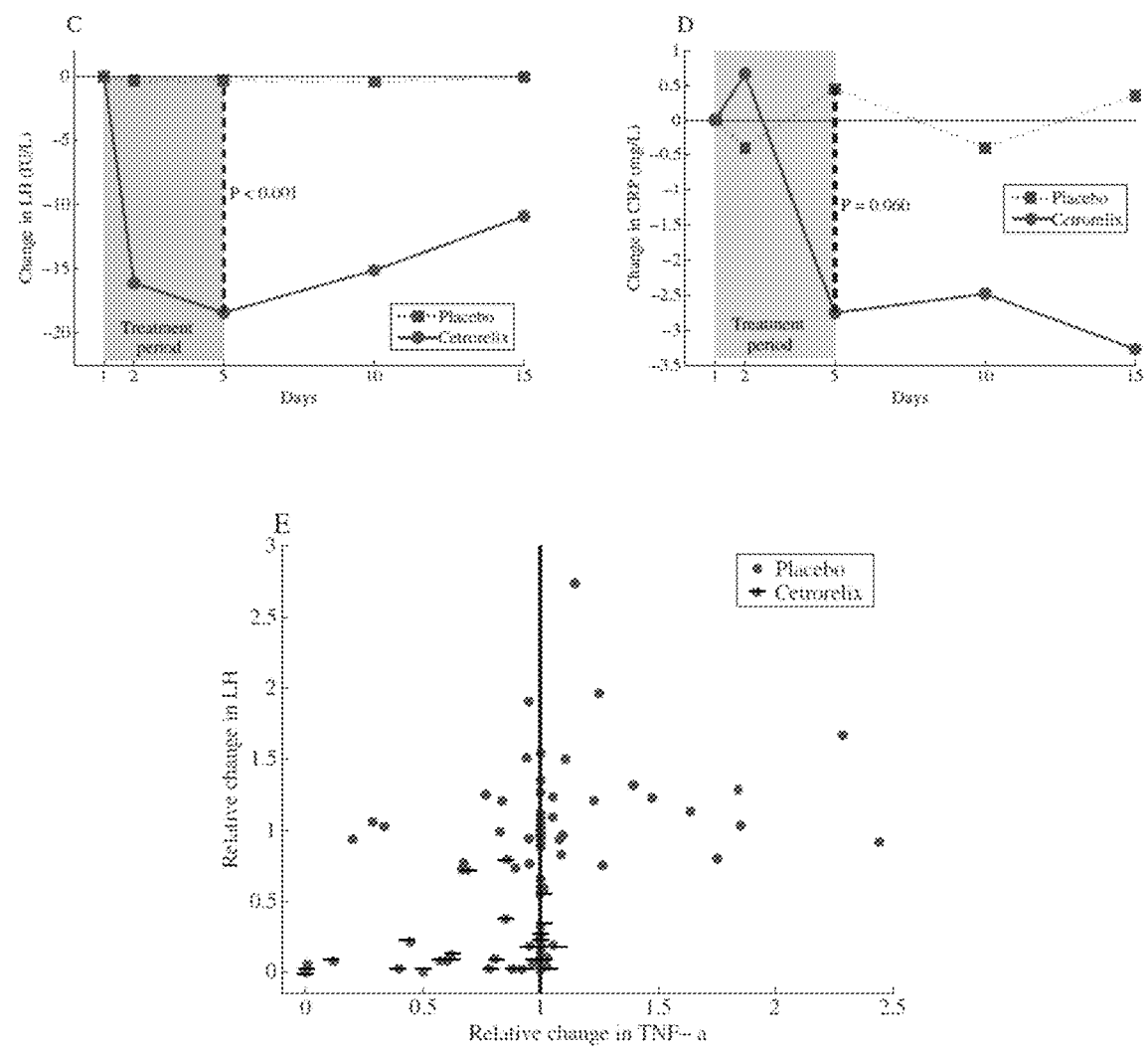
Figure 2:
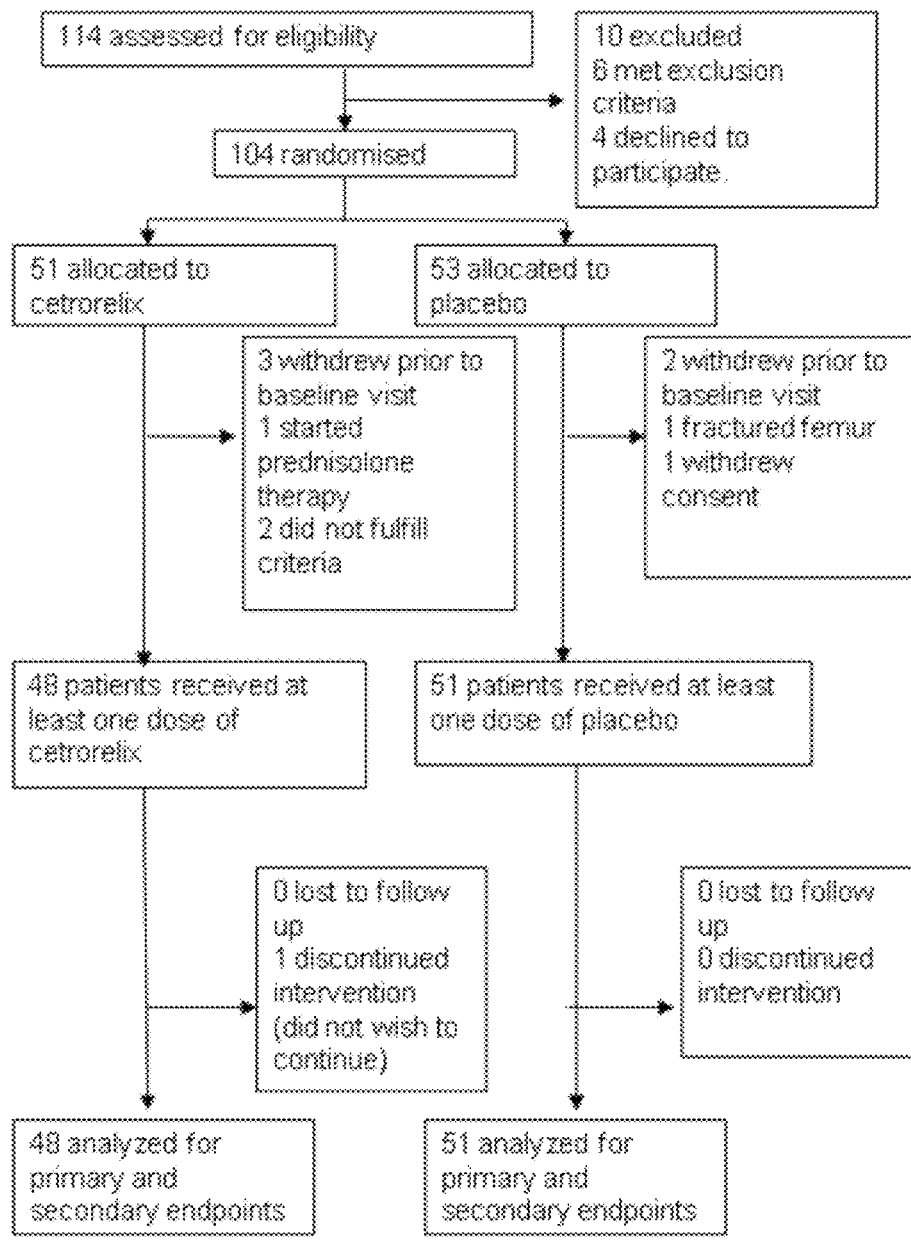
FIG. 2 shows a flow chart of the study design.

To facilitate an understanding of the present invention, a number of terms and phrases are defined below:

As used herein, the term "subject" refers to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

As used herein, the term "non-human animals" refers to all non-human animals including, but not limited to, vertebrates such as rodents, non-human primates, ovines, bovines, ruminants, lagomorphs, porcines, caprines, equines, canines, felines, ayes, etc.

As used herein, the term "sample" is used in its broadest sense. In one sense, it is meant to include a specimen or culture obtained from any source, as well as biological and environmental samples. Biological samples may be obtained from animals (including humans) and encompass fluids, solids, tissues, and gases. Biological samples include blood products, such as plasma, serum and the like. Environmental samples include environmental material such as surface matter, soil, water, crystals and industrial samples. Such examples are not however to be construed as limiting the sample types applicable to the present invention.

As used herein, the term "drug" is meant to include any molecule, molecular complex or substance administered to an organism for diagnostic or therapeutic purposes, including medical imaging, monitoring, contraceptive, cosmetic, nutraceutical, pharmaceutical and prophylactic applications. The term "drug" is further meant to include any such molecule, molecular complex or substance that is chemically modified and/or operatively attached to a biologic or biocompatible structure.

As used herein, the term "purified" or "to purify" or "compositional purity" refers to the removal of components (e.g., contaminants) from a sample or the level of components (e.g., contaminants) within a sample. For example, unreacted moieties, degradation products, excess reactants, or byproducts are removed from a sample following a synthesis reaction or preparative method.

The terms "test compound" and "candidate compound" refer to any chemical entity, pharmaceutical, drug, and the like that is a candidate for use to treat or prevent a disease, illness, sickness, or disorder of bodily function (e.g., cancer). Test compounds comprise both known and potential therapeutic compounds. A test compound can be determined to be therapeutic by screening using screening methods known in the art.

DETAILED DESCRIPTION OF THE INVENTION

The present invention relates to methods for the treatment of rheumatoid arthritis. In particular, the present invention relates to methods of treating rheumatoid arthritis with GnRH antagonists in patients with high gonadotropin and/or GnRH levels.

Current treatments for rheumatoid arthritis include: non-steroidal anti-inflammatory drugs (NSAIDs), corticosteroids, gold therapy, methotrexate, tumor necrosis factor inhibitors such as etanercept (Enbrel®), adalimumab (Humira®), and infliximab (Remicade®), and other immunomodulatory and cytotoxic agents. While these treatments can be effective many require close supervision because of hazardous side effects. Response to treatment with these agents is variable and some patients still experience pain and joint degeneration. Thus, there is a need for additional forms of treatment that can treat rheumatoid arthritis and related diseases.

Rheumatoid arthritis (RA) may develop, flare, or subside during hormonal changes in the hypothalamic-pituitary-gonadal (HPG) axis; for example, during pregnancy, postpartum, menopause, or aromatase inhibition therapy (1-3). These observations have prompted research into the effects of gonadal hormones of the HPG axis, such as oestrogen and testosterone in RA; but the results have been inconclusive.

Hypothalamic and pituitary hormones of the HPG axis control gonadal hormones. Gonadal hormones in both sexes are stimulated by pituitary LH and FSH. LH and FSH secretion are stimulated by the hypothalamic, GnRH. GnRH, LH, and FSH have important physiological roles in both male and female reproduction. Therefore, these hormones may be involved in pathological processes in males as well as females.

Experiments conducted during the course of development of embodiments of the present invention demonstrated that GnRH-antagonism produced rapid anti-inflammatory effects in RA patients with high gonadotropin levels. Accordingly, embodiments of the present invention provide methods and uses of treating rheumatoid arthritis, comprising: a) identifying subjects that have increased levels of GnRH or gonadotropins relative to a reference level; and b) administering a GnRH antagonist or a to the subjects.

In some embodiments, subjects are women (e.g., post-menopausal women or women over age 40). In some embodiments, women are treated with a GnRH antagonist at a specific point in the menstrual cycle (e.g., midcycle when LH and FSH levels reach a high point). While not limited to a particular mechanism, it is contemplated that such treatment prevents premenstrual flare ups of RA symptoms. In some embodiments, subjects are men over age 40 (e.g., over age 50, 60, or 70).

In some embodiments, the patient population is defined as negative for CCP antibodies. In some embodiments, the patient population is defined at DMARD and/or TNF non responders. In some embodiments, the patient population is patients not taking concomitant therapy.

In some embodiments, the patient population is defined as subjects with increased levels of GnRH or gonadotropins (e.g., one or more of oestradiol, testosterone, LH, and/or FSH) levels relative to a reference level. The clinically normal levels of LH and FSH vary based on age, gender, and menopausal status. For example, in some embodiments, the clinically normal levels for LH are as follows: adult male: 1.8-12.0 mIU/L; adult female premenopausal: follicular: 1-18 mIU/dL; mid-cycle: 20-105 mIU/mL; luteal: 0.4-20.0 mIU/mL; postmenopausal: 15.0-62.0 mIU/mL. In some embodiments, the clinically normal levels for FSH are as follows: adult male: 1.5-12.4 mIU/mL; adult female: premenopausal: follicular—1.0-8.8 mIU/dL. mid-cycle—4.0-25.0 mIU/mL. luteal—1.0-5.1 mIU/mL; postmenopausal: 16.7-134.8 mIU/mL. In some embodiments, the reference levels for the patient population to be treated are within or higher than the clinically normal levels defined above. In some embodiments, the reference levels are different for different ages, genders, and menopausal status patients.

While not limited to a particular reference level, in some embodiments, subjects with increased levels of GnRH or gonadotropins have LH and/or FSH levels above 15 IU/L and/or 16.7 IU/L, respectively (e.g., e.g., approximately LH>17.3 IU/L and/or FSH>34.6 IU/L) as determined by any suitable assay.

In some embodiments, subjects to be treated do not have levels of GnRH or gonadotropins below the reference level (e.g., as defined above). For example, in some embodiments, the methods described herein specifically exclude treatment of subjects with levels of GnRH or gonadotropins below the reference level. In some embodiments, the identifying comprises performing a quantitative diagnostic assay.

The present invention is not limited to a particular GnRH antagonist. In some embodiments, GnRH antagonist are small molecules, peptides (e.g., comprising one or more synthetic amino acids), peptide mimetics, and the like. Examples include, but are not limited to, cetrorelix, elagolix, ganirelix, abarelix, degarelix, detirelix, iturelix, ozarelix, prazarelix, ramorelix, or teverelix. Exemplary non-peptide (e.g., small molecule) GnRH antagonists are described, for example, in Armer et al., Curr Med Chem. 2004 November; 11(22):3017-28; Anderes et al., J Pharmacol Exp Ther. 2003 May; 305(2):688-95. Epub 2003 Jan. 24; Hauze et al., Bioorganic & Medicinal Chemistry Letters, Volume 19, Issue 7, 1 Apr. 2009, Pages 1986-1990; each of which is herein incorporated by reference in its entirety. Other small molecules GnRH antagonists are under development at Neurocrine Biosciences, San Diego, Calif.

In some embodiments of the present disclosure, the GnRH antagonists include classic pharmaceutical preparations. Administration of these compositions according to the present disclosure is via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection.

The GnRH antagonists may also be administered parenterally or intraperitoneally or intratumorally. Solutions of the active compounds as free base or pharmacologically acceptable salts are prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The present invention further provides the use of a GnRH antagonist in the treatment of rheumatoid arthritis in a subject that has increased levels of GnRH or gonadotropins relative to a reference level.

In some embodiments, the GnRH or gonadotropin antagonist is administered in combination with an additional treatment (e.g., treatments known to be useful in the treatment of rheumatoid arthritis). Examples of such agents include, but are not limited to, disease-modifying antirheumatic drugs (e.g., leflunomide, methotrexate, sulfasalazine, hydroxychloroquine), biologic agents (e.g., rituximab, infliximab, etanercept, adalimumab, golimumab), nonsteroidal anti-inflammatory drugs (e.g., ibuprofen, celecoxib, ketoprofen, naproxen, piroxicam, diclofenac), analgesics (e.g., acetaminophen, tramadol), immunomodulators (e.g., anakinra, abatacept), and glucocorticoids (e.g., prednisone, methylprednisone).

The additional agent can be an agent effective in treating arthritis (e.g., TNF-α inhibitors such as anti-TNF α monoclonal antibodies (such as REMICADE®, CDP-870 and HUMIRA™ (adalimumab) and TNF receptor-immunoglobulin fusion molecules (such as ENBREL®)(entanercept), IL-1 inhibitors, receptor antagonists or soluble IL-1R α (e.g. KINERET™ or ICE inhibitors), nonsteroidal anti-inflammatory agents (NSAIDS), piroxicam, diclofenac, naproxen, flurbiprofen, fenoprofen, ketoprofen ibuprofen, fenamates, mefenamic acid, indomethacin, sulindac, apazone, pyrazolones, phenylbutazone, aspirin, COX-2 inhibitors (such as CELEBREX® (celecoxib), VIOXX® (rofecoxib), BEXTRA® (valdecoxib) and etoricoxib, (preferably MMP-13 selective inhibitors), NEUROTIN®, pregabalin, sulfasalazine, low dose methotrexate, leflunomide, hydroxychloroquine, d-penicillamine, auranofin, parenteral or oral gold), rituximab, roactemera, or orencia. The additional agents to be co-administered can be any of the well-known agents in the art, including, but not limited to, those that are currently in clinical use.

EXAMPLES

The following examples are provided in order to demonstrate and further illustrate certain preferred embodiments and aspects of the present invention and are not to be construed as limiting the scope thereof.

Example 1

Methods

In this randomized, double-blind, placebo-controlled, single-centre study, males and females aged ≥18 years with RA according to the 1987 revised American College of Rheumatology (ACR) criteria, and with a 28-joint Disease Activity Score based on C-reactive protein (DAS28-CRP)> 3.2 were enrolled.

Ethical committee approval was obtained. A blinded independent committee, the Oslo University Hospital Data Monitoring Committee, regularly reviewed source documents against case record forms. Safety and efficacy visits, with blood sampling, were between 0730 and 0930 h on days 1 (baseline), 2, 3, 4, 5 (visit 5a), 10, and 15. There was an additional visit (visit 5b) between 1930 and 2130 h when maximum GnRH suppression was anticipated. Using computer-generated allocation, patients were randomly assigned 1:1 to cetrorelix (5 mg/day s.c. on days 1 and 2, 3 mg/day on days 3-5) or corresponding volumes of placebo. The cetrorelix doses were chosen to achieve rapid reductions in GnRH, LH, a surrogate marker for GnRH, and FSH. TNF-α was measured using multiplex technology with a high sensitivity (0.5 pg/mL) assay.

The predefined primary end-point was the baseline adjusted between-group difference in DAS28-CRP by visit 5b. Predefined secondary end-points included the baseline adjusted between-group difference inTNF-α, ACR20/50/70 responses, European League Against Rheumatism (EULAR) responses, DAS28-CRP <2.6 and ≤3.2, and adverse events. Continuous end-points were assessed with regression using day 5 as the response variable, and treatment and baseline measurement as covariates (ANCOVA). No adjustments for multiple analyses were made because of the highly correlated variables. Statistical tests were twosided (α ¼0.05) using Stat12/StatXact9, and performed by an offsite statistician who received the locked database from the blinded investigators, and the allocation key from the offsite central office.

Detailed Inclusion and Exclusion Criteria

Patients had a disease-activity score based on 28 joint count (DAS28)>3.2, with an active disease defined as at least 2 of the following criteria: ≥6 painful joints, ≥3 swollen joints, erythrocyte sedimentation rate (ESR) ≥20 mm/h or a C-reactive protein (CRP) ≥10 mg/L.

Menstruating women could only enter the study in the early follicular phase of their menstrual cycle. The concomitant use of stable doses of disease-modifying anti-rheumatic drugs (DMARDs) for at least 8 weeks, stable prednisolone ≤7.5 mg daily for at least 4 weeks, and stable non-steroidal anti-inflammatory drugs (NSAIDs) for at least 2 weeks was allowed if these doses were continued throughout the study. Key exclusion criteria were as follows: pregnancy or breast-feeding females; corticosteroid injections within the trial or 4 weeks prior to screening; biological agents were not permitted during the trial or within 4 weeks prior to inclusion in the trial (with the exception of infliximab or adalimumab which were not permitted within 3 months prior to inclusion in the trial; and rituximab which was not permitted within 6 months prior to inclusion in the trial). A history of hormone-dependent cancers ever or non-hormone-dependent cancers within 5 years prior to screening: infections requiring intravenous antibiotic treatment within 30 days, or oral antibiotics within 14 days prior to enrolment; significant renal or hepatic impairment; and any treatment with hormone replacement therapy or oral contraception were also exclusion criteria.

During the first three months, patients with disease duration >36 months or patients taking concomitant NSAIDs and prednisiolone were also excluded. Due to slow recruitment, these stricter criteria were removed after the first 6 patients were enrolled. This change was not expected to bias the results, and allowed data generated by this trial to be generalized to a wider RA population.

TNF-α Assay

TNF-α was measured using a high sensitivity bead-based fluorescence immunoassay (Luminex Inc., Austin, Tex. USA) with multiplex technology according to the manufacturers' instructions. No significant variation was noted between duplicates for any sample. Identical lots of critical reagent, of negligible cross reactivity <2%, was supplied by Biorad, Hercules, Calif., USA. Samples were assayed together within the same microplate on the same day. The assay sensitivity for TNF-α was 0.5 pg/mL. Due to its skewed distribution, the statistical analysis gives both the log and relative change (%) of TNF-α from baseline.

Hormone Assays

Non-competitive immunofluorometric assays were used for the quantitative determination of serum LH and FSH (Dissociation Enhanced Lanthanide Fluoroimmunoassay [DELFIA] kit, Turku, Finland). A competitive immunofluorometric assay was used for the determination of serum oestradiol (DELFIA kit, Turku, Finland). A competitive radioimmunoassay was used for the quantitative determination of serum testosterone (Orion Diagnostica. Espoo, Finland). A competitive luminoimmunoassay was used for the quantitative determination of serum cortisol (Immulite 2000, California, USA).

Further Statistical Analyses

The sample size calculation was based on a two-sided significance level of 5% and a power of 80%. Assuming a 10% dropout rate, the trial needed to enroll 49 patients per treatment group to detect a between-group difference of 0.6 DAS28 units with a standard deviation (SD) of 1.0.

Dichotomous endpoints were compared with the Pearson chi-squared test or the Suissa-Shuster exact unconditional test, depending on the distribution of expected values (Lydersen S, et al., Stat Med 2009; 28: 1159-75). The Newcombe hybrid score interval was used to estimate 95% confidence intervals (CI) for the difference between proportions (Fagerland M W, et al., Stat Methods Med Res 2011). No adjustments for multiple analyses were made, owing to the highly correlated variables. All clinical, biochemical, and safety data were analyzed by an intention-to-treat analysis. Only predefined endpoints are presented. The intention-to-treat population was predefined in the protocol as all randomized patients who received any injections of study drug. Missing values were <1% and could, as predefined, be imputed with the last observation carried forward. The assumptions of normality needed for analyses were approximately valid. The Spearman rank correlation coefficient (Spearman's rho) was used to estimate the association between pairs of continuous variables.

Results

The predefined intent-to-treat population comprised 99 patients who received at least one dose of cetrorelix (n = 48) or placebo (n = 51). Patients' baseline characteristics were similar between groups (Table 1).

DAS28-CRP reduction by day 5 was non-significantly greater in the cetrorelix group (0.82) compared with placebo (0.57) [between-group difference 0.26, 95% confidence interval (CI) −0.04 to 0.57, p = 0.091]. More patients achieved DAS28-CRP <2.6 (13% vs. 0%, p = 0.009) and ACR20 responses (40% vs. 18%; p = 0.015) by day 5 in the cetrorelix group compared with placebo. More patients reached ACR50/70 responses in the cetrorelix group (FIG. 1A).

Baseline TNF-α levels were comparable with other studies. Fifty-one of the 99 patients had detectable levels of TNF-α>0.5 pg/mL. TNF-α (log pg/mL) reduction was greater in the cetrorelix group (−0.58) than in the placebo group (−0.02) by day 5 (between group difference 0.55, 95% CI 0.08-1.01, p = 0.023) (FIG. 1B). TNF-α percentage change from baseline was also significantly reduced in the cetrorelix group compared with placebo by day 5 (−28.2% vs. 11.1%, p = 0.0028).

There was a significant correlation between the relative changes in both TNF-α and LH, a surrogate marker for GnRH, from baseline to day 5 [rho 0.48, p<0.001, n = 51 (both groups included). Relative changes between TNF-α and LH from baseline to day 5 are illustrated in FIG. 1E. There were weaker associations between relative changes in TNF-α and FSH, and TNF-α and oestradiol, but none between TNF-α and testosterone, or TNF-α and cortisol]. These findings were supported by a significant correlation between relative changes in DAS28-CRP and LH (p = 0.045), but not with FSH, oestradiol, testosterone, or cortisol (Table 2).

Non-significant reductions of CRP (day 5, p = 0.060, FIG. 1D) followed by erythrocyte sedimentation rate (ESR) (day 15, p = 0.051) were observed in the cetrorelix group compared to placebo. Cortisol changes were not significantly different between groups by day 5 (p = 0.80). In the cetrorelix group, DAS28-CRP reduction did not differ between prednisiolone users (n = 24) and non-users (n = 24) (p = 0.40).

LH, FSH, and inflammatory markers generally increased towards baseline levels after withdrawal of treatment; however, CRP levels remained lowered by day 15. (FIGS. 1B-1D).

Adverse events arose at similar frequencies in both groups.

Cetrorelix Onset and Offset Effect

LH and FSH remained stable in the placebo group (FIG. 1C shows change from baseline in LH). Although LH and FSH were reduced as early as day 2 in patients allocated to cetrorelix, there were no significant changes in clinical endpoints compared with patients allocated to placebo until maximal suppression of LH and FSH by day 5. By day 10, LH and FSH increased towards baseline levels after cessation of cetrorelix, with further increases towards baseline by day 15. The same trend was observed with DAS28CRP and with secondary endpoints. No variables in the cetrorelix group exceeded baseline levels after drug cessation. This rapid offset effect was expected owing to the short half-life of cetrorelix.

Core Set Measures

Each core set measure of disease activity showed non-significant greater improvements in the cetrorelix group compared with the placebo group except for the physician global assessment which was equally reduced in both groups.

Significant improvements in key secondary end-points, representing important disease activity markers, indicate that pathways targeted by GnRH are beneficial in rheumatoid arthritis. The data indicate that these pathways may involve TNF-α as a key molecule. As TNF-α inhibition is a common mode of action in RA therapy, antagonizing GnRH may have substantial therapeutic potential.

GnRH antagonists are used in other indications with a good safety profile over longer periods, and no serious side-effects were observed in this study. The observed changes in disease activity and TNF-α may be due to direct cellular effects of GnRH, or indirect effects through other hormones. Although the exact mechanisms are unknown, the highly significant association between changes in LH, a surrogate marker for GnRH, and TNF-α indicates there is a close relationship between endocrinological and immunological responsiveness to GnRH.

While the present disclosure is not limited to a particular mechanism for TNF-α inhibition and antiinflammatory effects, it is contemplated that the direct effects of GnRHon T cells, through binding of GnRH to its receptor on T cells is a mechanism for TNF-α inhibition. Human peripheral T cells can secrete GnRH, which acts upon these T cells in a cytokine-like way, stimulating T-cell proliferation and maturation (Chen A, et al., Nat Med 2002; 8:1421-6; Azad N, et al., Endocrinology 1993; 133:215-23; Morale M C, et al., Endocrinology 1991; 128:1073-85). A second mechanism may be through the effects of GnRH on B cells. GnRH administration led to increased immunoglobulinG levels in diabetes-prone rats (Jacobsen J D, et al., J Allergy Clin Immunol 1999; 104:653-58). Few data exist on the effects of GnRH on other immune cells. Indirect mechanisms include LH reduction, as LH itself stimulates T-cell proliferation (Sabharwal P, et al., Biochem Biophys Res Commun 1992; 187:1187-92), or FSH reduction, as FSH stimulates macrophage TNF-α production (Iqbal J, et al., Proc Natl Acad Sci USA 2006; 103:14925-30).

The findings do not indicate that cetrorelix ameliorates disease activity by effects on cortisol or oestradiol. Increased risk of presenting symptoms of RA and flares of disease activity are associated with the postpartum period, menopause, and aromatase inhibitor therapy (Pikwer M, et al., Ann Rheum Dis 2012; 71:378-81; Tan A L, et al., Lancet Oncology 2008; 9:817-18), when LH and FSH increase. By contrast, RA amelioration is associated with pregnancy and fasting (Ostensen M, et al., Scand J Rheumatol 1983; 12:69-72; Kjeldsen-Kragh J, et al., Lancet 1991; 338:899-902), when LH and FSH decrease. The findings support that these relationships are related to changes in upstream hormones (GnRH, LH, or FSH) of the HPG axis rather than downstream gonadal hormones. This is also supported by a previous study, which showed that changes in disease activity and key cytokines, such as TNF-α, were significantly associated with changes in LH and FSH (but not with oestradiol, testosterone, prolactin, or cortisol) in RA (Kass A S, et al., Scand J Rheumatol 2010; 39:109-17). Women have more frequent and more substantial HPG axis fluctuations than men, which may contribute to an explanation of why RA is more frequent and severe in women than men.

In summary, antagonizing GnRH represents a novel mode of action for TNF-α inhibition with rapid anti-inflammatory effects in rheumatoid arthritis.

TABLE 1

Baseline characteristics.*

| | Cetrorelix (n = 48) | Placebo (n = 51) |
|---|---|---|
| Demographics | | |
| Age (years) | 54.9 ± 11.4 | 55.0 ± 11.7 |
| Female sex (%) | 73 | 71 |
| Disease duration (years) | 11.5 ± 10.6 | 12.0 ± 12.9 |
| Anti-CCP antibody positive, n (%) | 28 (58) | 35 (69) |
| Current smoker, n (%) | 13 (27) | 20 (39) |
| Clinical and laboratory measures | | |
| DAS28-CRP | 5.0 ± 1.0 | 5.2 ± 1.0 |
| CRP (mg/L) | 18.9 ± 24.5 | 17.3 ± 22.5 |
| ESR (mm/h) | 22.0 ± 18.3 | 25.8 ± 27.0 |
| TNF-α (pg/mL)† | 21.2 ± 291 | 49.6 ± 290 |
| LH (IU/L) | 20.4 ± 16.3 | 19.6 ± 16.3 |
| FSH (IU/L)‡ | 36.9 ± 30.0 | 32.9 ± 31.1 |
| Cortisol (nmol/L) | 392 ± 151 | 401 ± 200 |
| Current medication | | |
| None, n (%) | 11 (23) | 12 (24) |
| Stable NSAIDs, n (%) | 9 (19) | 14 (27) |
| Stable prednisolone ≤ 7.5 mg, n (%) | 24 (50) | 22 (43) |
| Stable DMARDs, n (%) | 19 (40) | 27 (53) |
| MTX | 16 (33) | 17 (33) |
| LEF | 2 (4) | 2 (4) |
| SSZ | 0 | 1 (2) |
| HCQ | 1 (2) | 2 (4) |
| MTX + SLZ | 0 | 3 (6) |
| MTX, SSZ, + HCQ | 0 | 2 (4) |
| Previous failure to DMARD and biologic therapy§ | | |
| Previous failure with DMAHDs, n (%) | 40 (83) | 45 (88) |
| One previous DMARD | 13 (27) | 13 (25) |
| Two previous DMARDs | 10 (21) | 9 (18) |
| Three or more previous DMARDs | 17 (35) | 23 (45) |
| Previous failure with biologies, n (%) | 21 (44) | 23 (45) |
| One previous biologic | 9 (19) | 9 (18) |
| Two previous biologies | 6 (13) | 3 (6) |
| Three or more previous biologics | 6 (13) | 11 (22) |

CCP, Cycle citrullinated peptide;
DAS28-CRP, 28-joint Disease Activity Score calculated with C-reactive protein levels;
ESR, erythrocyte sedimentation rate;
TNF-α, tumour necrosis factor-α;
LH, luteinizing hormone;
FSH, follicle-stimulating hormone;
NSAID, non-steroidal anti-inflammatory drug;
DMARD, desease-modifying anti-rheumatic drug;
MTX, methotrexate;
SSZ, sulfasalazine;
HCQ, hydroxychloroquine;
LEF, leflunomide.
*Values are given as mean ± standard deviation unless otherwise indicated.
†Data are median (IQR), based on delectable TNF-α values > 0.5 pg/mL; n = 21 (cetrorelix), n = 30 (placebo).
‡Based on detectable FSH values < 256 IU/L, n = 48 (cetrorelix), n = 50 (placebo).
§Previous failure includes inefficacy or intolerabilty.

TABLE 2

Correlations of relative changes from baseline to day 5 in TNF-α and hormones, and in DAS28-CRP and hormones.

| Variables* | n | Spearman's rho | p-value |
|---|---|---|---|
| TNF-α† and hormones | | | |
| Relative change in TNF-α related to relative change in LH | 51 | 0.48 | 0.0004 |
| Relative change in TNF-α related to relative change in FSH‡ | 50 | 0.30 | 0.034 |
| Relatwe change in TNF-α related to relative change in oestradiol | 51 | 0.30 | 0.035 |
| Relative change in TNF-α related to relative change in testosterone | 51 | 0.22 | 0.12 |
| Relative change in TNF-α related to relative change in cortisol | 51 | −0.12 | 0.40 |
| DAS2B-CHP and hormones | | | |
| Relative change in DAS28-CRP related to relative change in LH | 99 | 0.20 | 0.045 |
| Relative change in DAS28-CRP related to relative change in FSH‡ | 98 | 0.13 | 0.22 |
| Relative change in DAS28-CRP related to relative change in oestradiol | 99 | 0.01 | 0.94 |
| Relative change in DAS28-CRP releted to relative change in testosterone | 99 | <0.01 | 0.98 |
| Relative change in DAS28-CRP releted to relative change in cortisol | 99 | 0.10 | 0.32 |

TNF-α, Tumour necrosis factor-α;
DAS28-CRP, 28-joint Disease Activity Score calculated with C-reactive protein levels;
LH, luteinizing hormone;
FSH, follicle-stimulating hormone.
*Relative change calculated as the change by day 5 divided by the baseline level.
†Based on detectable TNF-α values > 0.5 pg/mL; n = 21 (cetrorelix), n = 30 (placebo).
‡Based on delectable FSH values < 256 IU/L; n = 48(cetrorelix), n = 50 (placebo).

TABLE 3

Adverse effects

| Event | Cetrotide, N = 48 n (percent) | Placebo, N = 51 n (percent) |
|---|---|---|
| Headache | 2 (4.2) | 6 (11.8) |
| Injection site discomfort | 3 (6.3) | 0 |
| Nausea | 0 | 3 (5.9) |
| Menstrual spotting | 2 (4.2) | 0 |
| Hot flushes | 2 (4.2) | 0 |
| Toothache | 0 | 1 (2.1) |
| Urinary tract infection | 1 (2.1) | 0 |
| Nasopharyngitis | 1 (2.1) | 0 |

*There were no significant between-group differences.

Example 2

Methods

AGRA is a proof-of-concept, investigator-initiated, randomized, double-blind, placebo-controlled trial assessing the effects of GnRH antagonism in RA patients (Kass A S, et al., Scand J Rheumatol Epub ahead of print 1 Nov. 2013); carried out at Betanien Hospital, Norway; ClinicalTrials.gov number NCT00667758. Post hoc analyses is described herein.

Patients

Key inclusion criteria for AGRA were males or females aged ≥18 years with RA that had been diagnosed on the basis of the American College of Rheumatology (ACR) 1987 revised criteria (Arnett F C, et al., Arthritis Rheum 1988; 31:315-24); with active, and moderate or severe disease defined as a Disease Activity Score for 28-joint counts based on C-reactive protein (Wells G, et al., Ann Rheum Dis 2009; 68:954-60) (DAS28-CRP) >3.2 and at least two of the following criteria: ≥6 painful joints, ≥3 swollen joints, ESR ≥20 mm/h, and a C-reactive protein ≥10 mg/L). Prednisolone ≤7.5 mg/day was permitted if stable for at least 4 weeks prior to baseline; NSAIDs were permitted if stable for at least 2 weeks prior to baseline; and disease-modifying anti-rheumatic drugs (DMARDs) were permitted if stable for at least 8 weeks prior to baseline. Tumour necrosis factor-α (TNF-α) inhibitor or other biological agents were not permitted during the trial or within 4 weeks prior to inclusion. Infliximab/adalimumab was not permitted at least 3 months prior to inclusion; Rituximab was not permitted at least 6 months prior to inclusion. Intramuscular, intra-articular or intravenous corticosteroids; any hormone replacement therapy; or oral contraception was not permitted during the trial or within 4 weeks prior to inclusion.

During the first three months, patients with disease duration>36 months or patients taking concomitant NSAIDs and prednisolone were also excluded. Due to slow recruitment, these stricter criteria were removed after the first 6 patients were enrolled. This change was not expected to bias the results, and allowed data generated by this trial to be generalized to a wider RA population.

In these post hoc analyses, a subgroup of AGRA patients with high gonadotropin levels were examined. There is no established cut-off for high LH and/or FSH. Therefore, levels above the median were defined as high (e.g., LH>17.3 IU/L and FSH>34.6 IU/L).

Design

Visits were between 0730-0930 hours on days 1 (baseline), 2, 3, 4, 5, 10, and 15. On day 5, an additional visit (visit 5b) occurred between 1930-2130 hours when the greatest suppression of GnRH and gonadotropins was anticipated. Once a patient had been through the screening process and gave informed consent, the unmasked research nurse obtained randomisation information by calling an offsite central office with no clinical involvement in the trial (Clinical Research Centre, University of Oslo) which randomised the patient through computer generated allocation. Randomisation was in random block sizes and stratified for sex, assigning patients in a 1:1 ratio to receive either daily subcutaneous injections of cetrorelix acetate (5 mg/d for the first two days and 3 mg/d for the following 3 days, in total 5 consecutive days of medication) or corresponding volumes of saline placebo. These cetrorelix doses were chosen to achieve rapid reductions in GnRH, LH, a surrogate marker for GnRH, and FSH.

This unmasked research nurse was responsible for the preparation of cetrorelix and placebo injections at the nurses' station away from the patient's treatment room.

Once the study drug was prepared in the syringe, the cetrorelix injection (a colourless, odourless liquid) was indistinguishable from the placebo injection. The unmasked research nurse did not do any trial assessments. The research nurses successfully maintained masking of all other study personnel (including healthcare providers and outcome assessors) and participants. The research nurse administered the study drug and kept a written locked record of what drug was given. This record was not shared until the database lock had occurred after the last patient's final visit.

Any concomitant therapy had to be stable prior to and during the study, and taken at the same time of day. Blinded laboratory assessments were performed in batches after the study's completion.

The Regional Committee for Medical and Health Research Ethics (South-East Region) approved the study protocol. All participants provided informed consent according to the Declaration of Helsinki. An independent data-monitoring committee monitored the trial for scientific integrity. The first author wrote all manuscript drafts and all the authors revised the manuscript for intellectual content. All the authors made the decision to submit the manuscript for publication and vouch for the completeness and accuracy of the data and analyses and for the fidelity of the study to the protocol.

Outcomes

The protocol-specified primary and secondary intention-to-treat endpoints of the original AGRA trial were analyzed in these post hoc analyses. The primary endpoint was the baseline-adjusted between-group difference in DAS28-CRP (Wells et al., supra) by day 5b. Secondary endpoints included the baseline-adjusted between-group difference in cytokines, proportions of patients achieving at least a 20%, 50%, and 70% improvement on the ACR scale (Felson D T, et al., Arthritis Rheum 1995; 38:727-35), categorical DAS28-CRP (European League Against Rheumatoid Arthritis [EULAR]) responses (Wells et al., supra; van Gestel A M, et al., Arthritis Rheum 1996; 39:34-40), DAS28-CRP≤3.2 (Wells et al., supra), DAS28-CRP<2.6 (Wells et al., supra), and the incidence of adverse events. Protocol-specified DAS28 outcomes were preferentially CRP-based rather than erythrocyte sedimentation rate (ESR)-based, as CRP usually changes before ESR. Based on the results from the case-control study (Kass A S, et al., Scand J Rheumatol 2010; 39:109-17), TNF-α, interleukin-1β, interleukin-2 and interleukin-10 levels were assesed. Multiplex technology (Luminex Inc., Austin, Tex.) measured these serum cytokines using high-sensitivity assays (sensitivities <0.5 pg/mL, allowing the detection of very low concentrations of cytokines) and identical lots of critical reagent of negligible cross-reactivity <2%, according to manufacturers' instructions (Bio-Rad, Hercules, Calif.). No significant variation was noted between duplicates for any sample. To enable intention-to-treat analyses with all patients N=53, non-detectable values were set at the lower limit of detection for cytokines, as is common for CRP values. Values were above the lower limit of detection in 22 of 53 patients for tumor necrosis factor-α, 11 of 53 patients for interleukin-1β, 14 of 53 patients for interleukin-2, and 26 of 53 patients for interukin-10.

Statistical Analysis

The original power calculation is previously reported (Kass A S, et al., Scand J Rheumatol Epub ahead of print 1 Nov. 2013). Baseline-adjusted between-group differences for all continuous endpoints were assessed with the use of analysis-of-covariance using outcome measurements at pre-defined time points as response variables, and treatment and baseline measurements as covariates. Dichotomous endpoints were compared with the Pearson chi-square test or Suissa-Shuster exact unconditional test, depending on expected-value distribution (Lydersen S, et al., Stat Med 2009; 28:1159-75). No adjustments for multiple analyses were made, owing to highly correlated endpoints. Due to skewed distributions, between-group changes of natural log-transformed cytokine levels from baseline were compared.

The intention-to-treat population was predefined as all randomised patients who received any study-drug injections. Missing values were <1% and could, as predefined, be imputed with the last-observation-carried-forward. The assumptions of normality needed for analyses were approximately valid. All statistical tests were two-sided ($\alpha=0.05$) and performed with Stata 12 and StatXact 9. Analyses were performed by an offsite statistician who received locked databases from blinded investigators and laboratories, and the allocation key from the offsite central office.

Results

Figure 3:
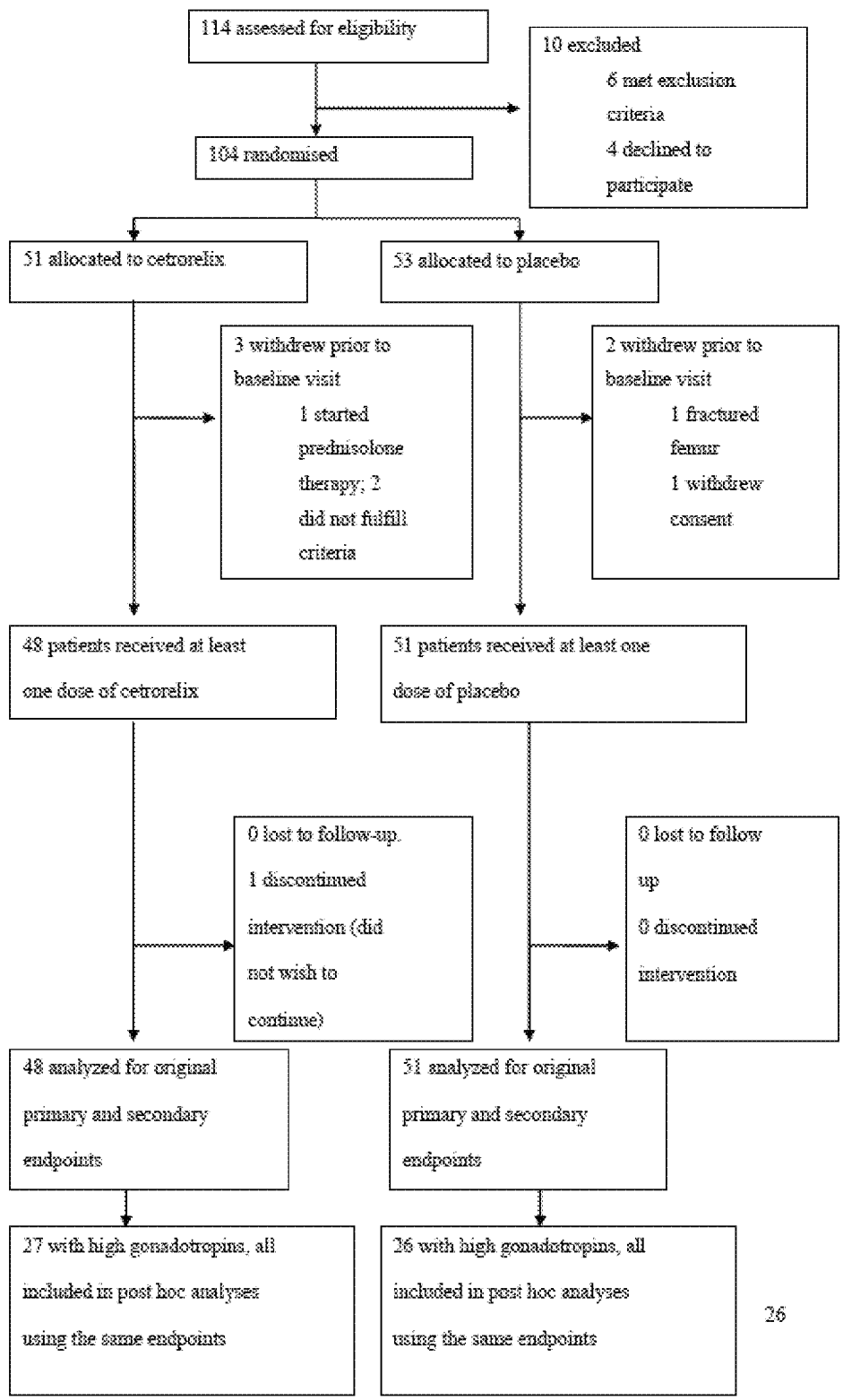
FIG. 3 shows a flow chart of a clinical trial described in Example 2.

Patient's visits were performed between Aug. 1, 2008 and Jun. 11, 2011. Compared to the whole AGRA group, patients with high gonadotropin levels were older and almost all were females. Except for this, there were no significant differences in baseline characteristics or concomitant therapy, between all groups (Table 4). For the remainder of the example, when referring to patients in the cetrorelix and placebo groups, the 53 patients with high gonadotropin levels (FIG. 3) are indicated, unless otherwise specified.

DAS28-CRP

DAS28-CRP decreased with cetrorelix by day 5 (−1.0; 95% CI −1.3 to −0.67) compared with placebo (−0.40; 95% CI −0.71 to −0.19); baseline-adjusted between-group difference 0.53, 95% CI 0.13 to 0.93; P=0.010.

Figure 4:
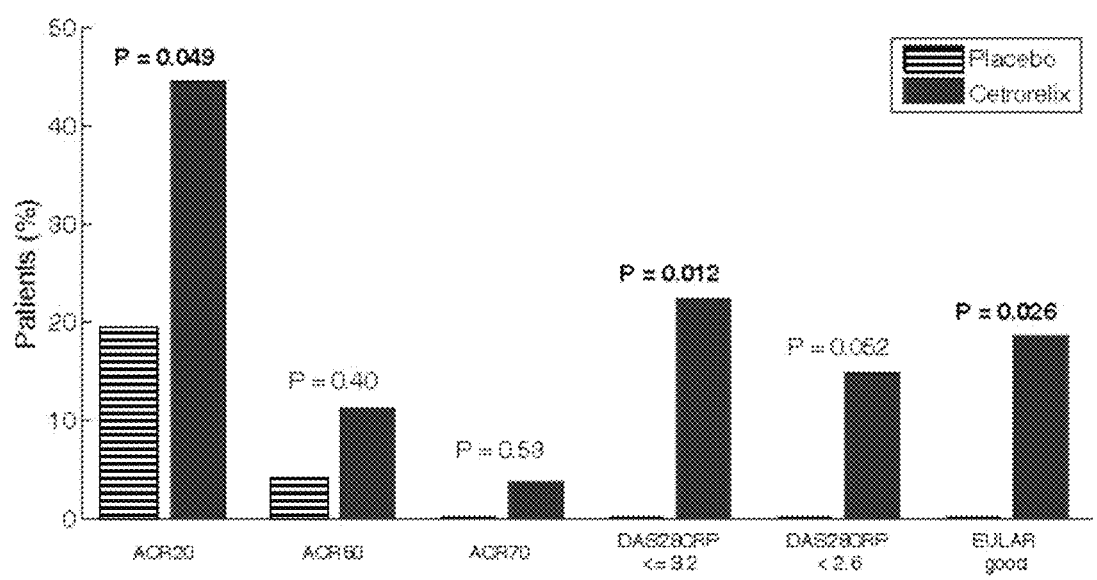
FIG. 4 shows the percentage of patients achieving at least a 20%, 50%, 70% improvement in the American College of Rheumatology scale (ACR20, ACR50, and ACR70 respectively), the percentage of patients achieving≤3.2 on the Disease Activity Score for 28-joint counts, based on C-reactive protein ([DAS28-CRP≤3.2], in which scores range from 2 to 9, with higher scores indicating more disease activity), the percentage of patients achieving DAS28-CRP<2.6, European League Against Rheumatism 'Good-Responses' (EULAR good). All patients, N=53, are included in these intention-to-treat analyses.

More patients achieved DAS28-CRP≤3.2 (22% vs. 0%, P=0.012) and DAS28-CRP<2.6 (15% vs. 0%; P=0.052) by day 5 with cetrorelix, compared with placebo (FIG. 4).

Among patients in both the cetrorelix and placebo groups combined, change in DAS28-CRP was associated with change in LH (Spearman-rho-0.33; 95% CI 0.065 to 0.56; P=0.016) and FSH (rho=0.32; 95% CI 0.046 to 0.55; P=0.023) but not with change in cortisol, oestradiol or testosterone.

ACR and EULAR Responses

By day 5, more patients achieved ACR20 responses (44% vs. 19%; P=0.049) and EULAR 'Good-Reponses' (19% vs. 0%, P=0.026) with cetrorelix, compared with placebo (FIG. 4). More patients reached ACR50 and ACR70 responses with cetrorelix, although numbers were too small for valid conclusions.

CRP

Figure 5A:
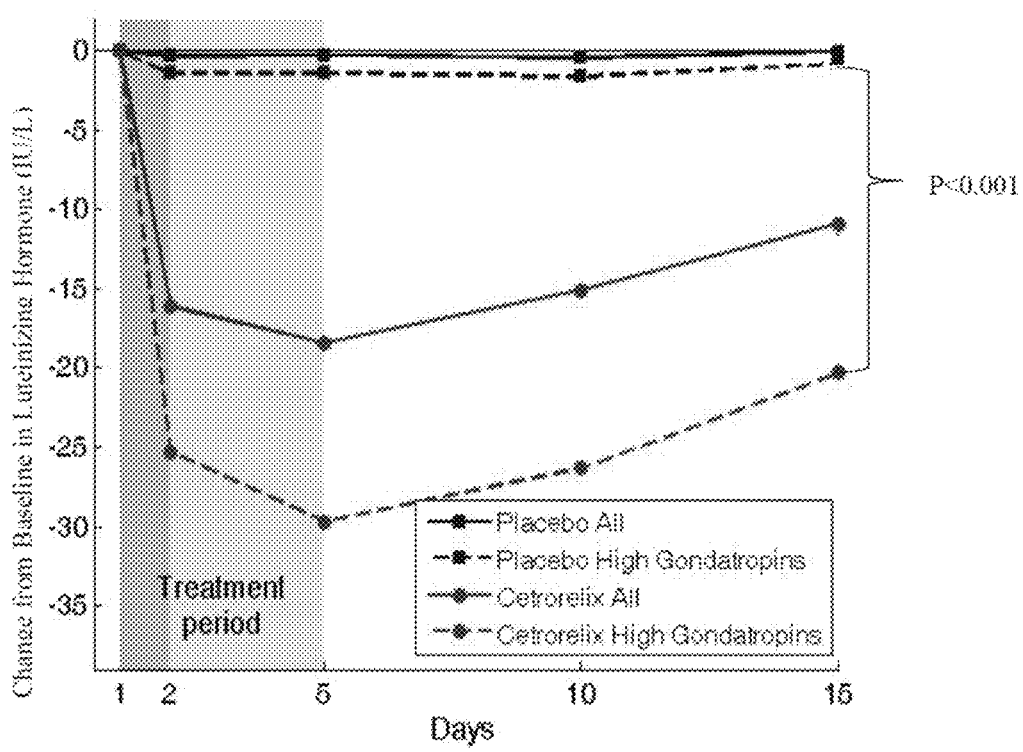
FIG. 5A-F shows change in hormonal and immunological variables from baseline.

CRP (mg/L) decreased with cetrorelix (−5.1), compared with an increase with placebo (0.85); between-group difference 5.45; 95% CI 0.22 to 10.7; P=0.042 by day 15 (FIG. 5A).

Cytokines

TNF-α (log pg/mL) significantly decreased with cetrorelix (−0.45), compared with an increase with placebo (+0.02) by day 15 (P=0.045). Interleukin-1β and interleukin-10 also significantly decreased with cetrorelix, compared with placebo (P=0.034 and P=0.020), and interleukin-2 decreased non-significantly with cetrorelix, compared with placebo (P=0.088) by day 15 (Table 5; FIG. 5B-E).

Notably with cetrorelix, the reduction of LH (a surrogate marker for GnRH) and all cytokines was greatest during the first two days when the highest doses of cetrorelix were given (FIG. 5A-E).

Onset and Offset

Although gonadotropin levels were decreased with cetrorelix already by day 2, there were no significant changes in clinical endpoints compared with placebo, until maximum gonadotropin suppression by day 5. As expected by day 10, gonadotropins increased after treatment withdrawal, increasing further towards baseline by day 15 (FIG. 5A). The same trend was observed with DAS28-CRP and secondary endpoints. Although this indicates that there was a rapid offset effect, interleukin-1β, interleukin-2 and interleukin-10 remained decreased, and TNF-α and CRP appeared to continue to decrease despite treatment withdrawal.

Cortisol

Cortisol (nmol/L) significantly decreased with cetrorelix, compared with placebo by day 5 (between-group difference 53.1, 95% CI 10.5 to 95.8, P=0.016). This reduction was not associated with patients' use of prednisolone. Furthermore, among patients who received cetrorelix, DAS28-CRP reduction was similar in prednisolone users (N=13) and non-users (N=14; P=0.73).

Adverse Events

Adverse events occurred in similar frequencies in both groups, and were mild (Table 6).

This study indicates that short-term treatment with a GnRH-antagonist has rapid disease ameliorating effects in RA patients with high gonadotropin levels. The original primary endpoint and several original key secondary endpoints were met. It is notable that a significantly greater proportion of patients achieved a DAS28-CRP≤3.2 (22% vs. 0%) and a EULAR 'Good-Response' (19% vs. 0%) on cetrorelix compared to placebo by day 5. There was also a trend towards a greater proportion of patients achieving DAS28-CRP<2.6 on cetrorelix compared to placebo (15% vs. 0%). Importantly, cetrorelix treatment resulted in significant improvements of objective biochemical endpoints, CRP, TNF-α, interleukin-1β and interleukin-10. GnRH antagonism may ameliorate RA activity through, at least in part, proinflammatory cytokine inhibition (which could consequently inhibit the secretion of the anti-inflammatory cytokine, interleukin-10 (Parry S L, et al., J Immunol 1997; 158:3673-81)).

Figure 5B:
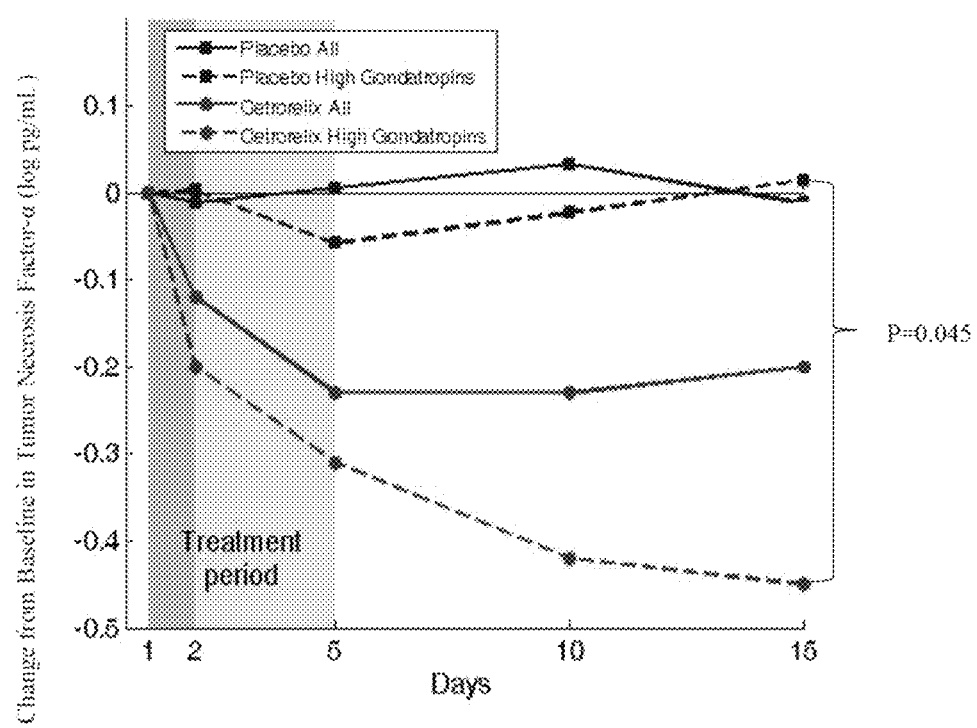
Figure 5C:
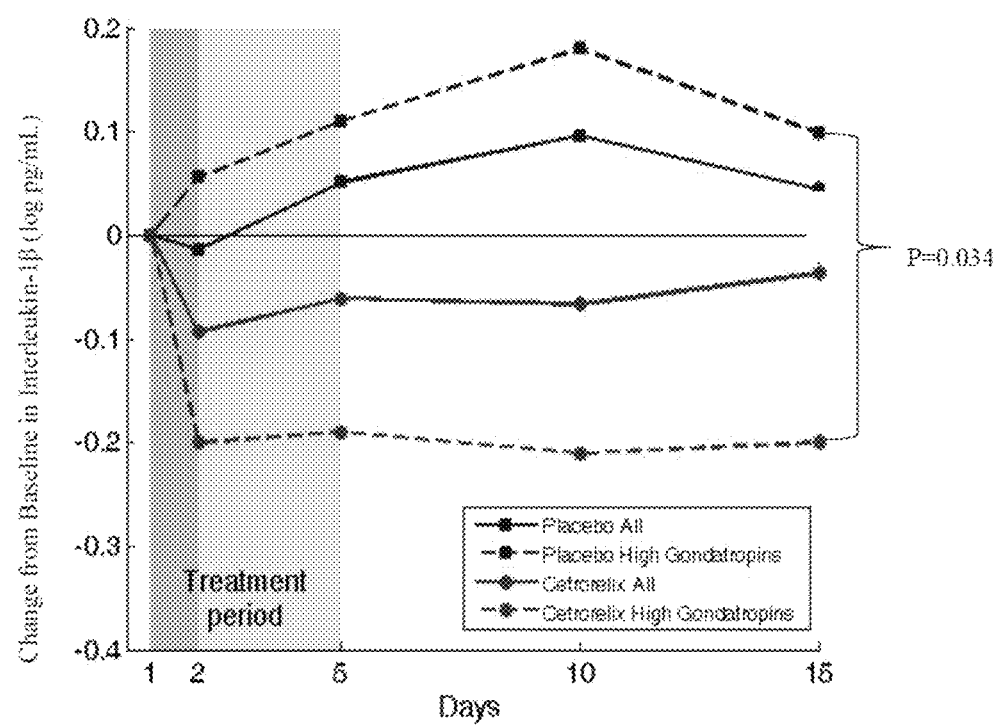
Figure 5D:
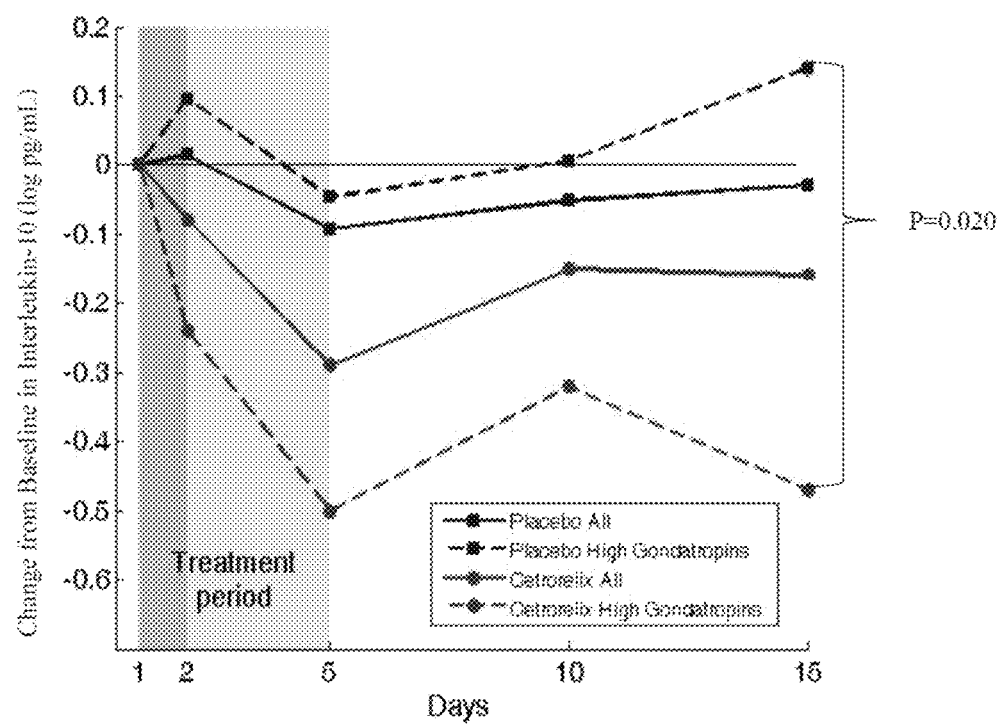
Figure 5E:
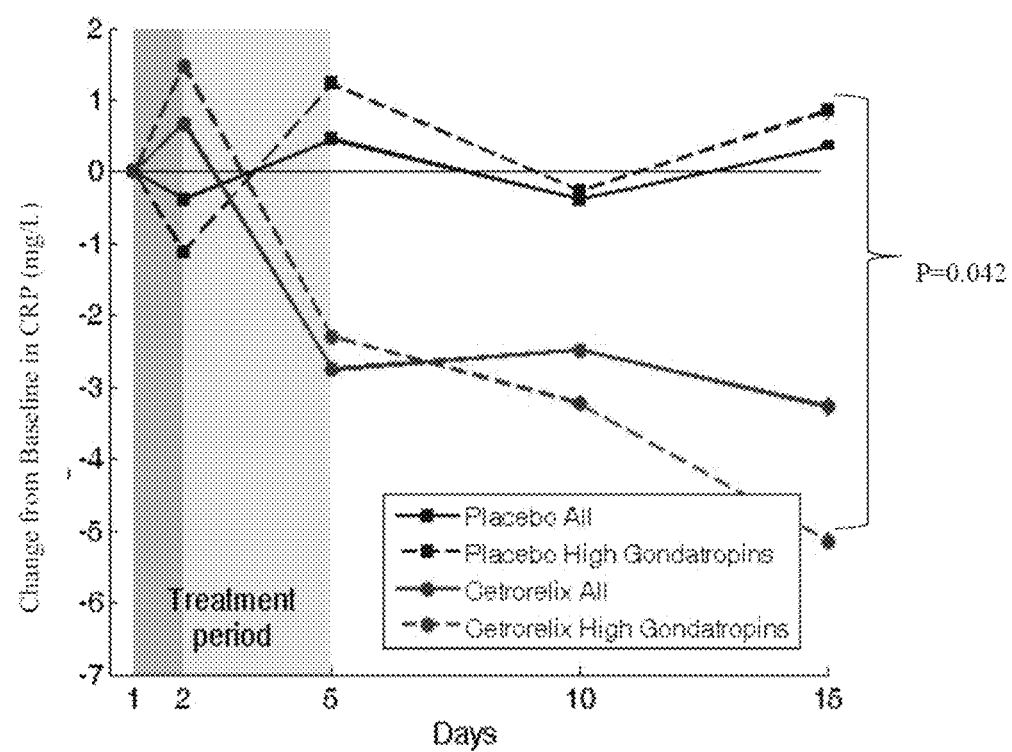
Figure 5F:
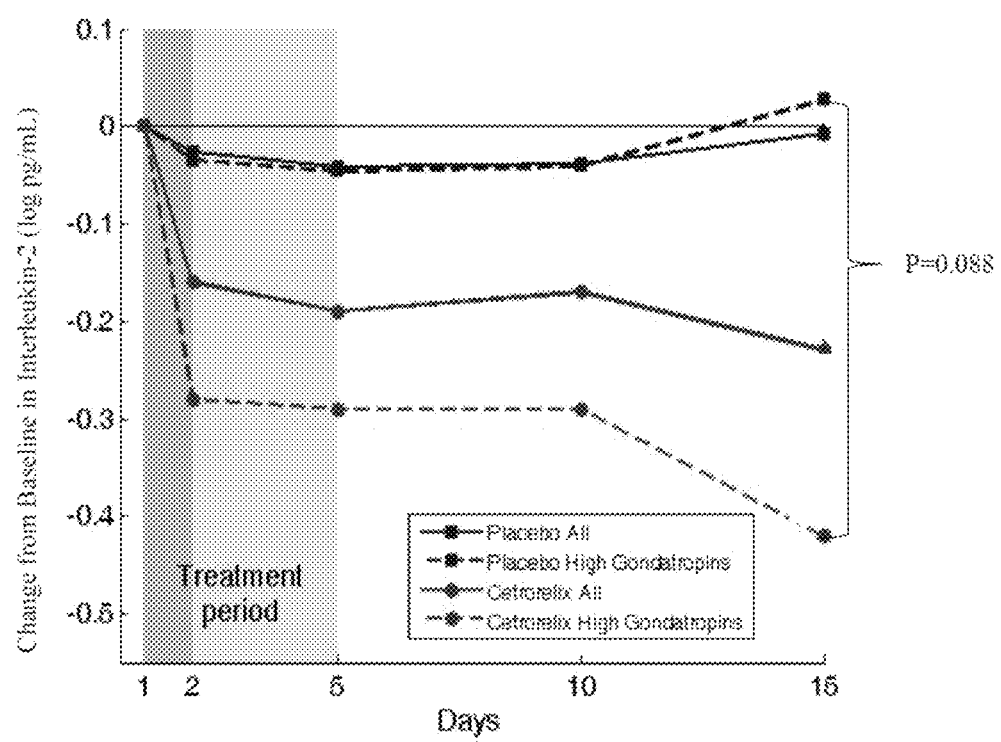

Compared to placebo, cetrorelix showed greater reductions of DAS28-CRP and cytokines in the high gonadotropin groups (N=53) versus the rest of the AGRA population (N=46) (FIG. 5B-3E). Thus, these findings indicate that GnRH-antagonism has a strong anti-inflammatory effect in RA patients with high gonadotropins.

It is not known whether the cytokine reductions due to cetrorelix treatment is mediated directly through GnRH or indirectly via downstream hormones such as gonadotropins. Cetrorelix has been shown to directly decrease pro-inflammatory cytokine gene expression through GnRH receptors in rats (Rick F G, et al., Prostate 2011; 71:736-47), and myeloma cells (Wen J, et al., Mol Cancer Ther 2011; 10:148-58). Therefore, it is not unlikely that cetrorelix reduces RA activity by down-regulating proinflammatory cytokine secretion via a direct effect on GnRH receptors on immune cells. The simultaneous reduction of cytokines, CRP, and disease activity in this study, might be explained, at least partially, through GnRH-receptor blockade on T cells. Peripheral T cells can secrete immunoactive GnRH, which acts upon these T cells through GnRH receptors, stimulating T-cell proliferation and maturation (Chen A, et al., Nat Med 2002; 8:1421-6; Azad N, et al., Endocrinology 1993; 133:215-23; Morale M C, et al., Endocrinology 1991; 128:1073-85; Chen H F, et al., J Clin Endocrinol Metab 1999; 84:743-50; Batticane N, et al., Endocrinology 1991; 129:277-86; Tanriverdi F, et al., J Endocrinol 2003; 176: 293-304). Another explanation may be through GnRH's effects on B cells. Indeed, GnRH administration led to increased immunologlobulin G levels in diabetes-prone rats (Ansari M A, et al., Endocrinology 2004; 145:337-42).

Cetrorelix significantly reduced gonadotropins, oestradiol, testosterone and cortisol compared to placebo. DAS28-CRP correlated positively with gonadotropins, but not with oestradiol, testosterone or cortisol. Thus, it is more likely that the observed anti-inflammatory effect is mediated by GnRH and/or gonadotropin reduction, rather than oestradiol, testosterone or cortisol reduction. These findings are supported by an earlier longitudinal case-control study, where changes in gonadotropins, but not oestradiol, testosterone, cortisol or prolactin, positively correlated with changes in proinflammatory cytokines and disease activity markers in RA patients, and not in controls (Kass A S, et al., Scand J Rheumatol 2010; 39:109-17). Furthermore, it has been demonstrated that RA flares are associated with gonadotropin elevations, but not with prolactin, cortisol or testosterone variations (Gordon D, et al., Br J Rheumatol 1988; 27:440-44).

Cetrorelix significantly reduced cortisol, compared to placebo. The reduction in cortisol could be a reflection of decreased inflammatory activity, as less cortisol would then be required to counteract the proinflammatory environment. However, the reduction in cortisol may be a result of a direct effect of GnRH either centrally, i.e. the hypothalamus or pituitary, or peripherally upon adrenal gland cells. The upstream hypothalamic-pituitary-gonadal hormones, GnRH and LH, directly stimulate cortisol secretion through GnRH and LH receptors in the adrenal cortex (Alevizaki M, et al., Eur J Endocrinol 2006; 154:875-81; Kero J, et al., J Clin Invest 2000; 105:633-41; Bernichtein S, et al., Trends Endocrinol Metab 2008; 19:231-8). Therefore, decreases in GnRH and LH may directly decrease cortisol secretion. In turn, due to negative feedback, cortisol directly inhibits hypothalamic GnRH and pituitary gonadotropins through glucocorticoid receptors on hypothalamic and pituitary cells (Calogero A E, et al., J Endocrinol Invest 1999; 22:666-70; Breen K M, et al., Endocrinology 2005; 146:2107-15).

Furthermore, it is possible that increases of GnRH and LH directly result in the increase of cortisol in the menopausal transition and PCOS (Alevizaki M, et al., supra; Kero et al., supra). Both the menopausal transition and PCOS are associated with an increased susceptibility to RA (Pikwer M, et al., Ann Rheum Dis 2012; 71:378-81; Merlino L A, et al., Semin Arthritis Rheum 2003; 33:72-82). Thus, it is speculated that increases in anti-inflammatory cortisol could be partially in response to increases in proinflammatory upstream hypothalamic-pituitary-gonadal hormones, and for some individuals, the cortisol rise may not protect against the development of RA.

GnRH pulsatility is also regulated by an endogenous circadian clock (Merlino L A, et al., Semin Arthritis Rheum 2003; 33:72-82). One study indicates that due to the circadian rhythm of the hypothalamic-pituitary-gonadal axis, there is an intrinsic increase of LH under GnRH-antagonist therapy at 0200-0300 AM (Merlino L A, et al., Semin Arthritis Rheum 2003; 33:72-82). This LH increase precedes the rise of proinflammatory interleukin-6 (Perry M G, et al. Ann Rheum Dis 2009; 68:63-8) and possibly rises of other cytokines, and also precedes maximum RA activity during the 24-hour period (Harkness J A, et al. Circadian variation in disease activity in rheumatoid arthritis. BMJ 1982; 284:551-4). The intrinsic increase in LH also occurs before the morning increases in cortisol, and may itself be involved in triggering a cortisol rise. Another study showed that giving glucocorticoids to RA patients suppressed interleukin-6 production, but the diurnal variation of interleukin-6 remained, indciating glucocorticoids alone could not wholly explain the inflammatory diurnal variation (Arvidson N G, et al., Ann Rheum Dis 1994; 53:521-4). Therefore, RA patients may have a centrally acting proinflammatory stimulus, for example, upstream hypothalamic-pituitary-gonadal hormones. Notably, these hormones can also be secreted peripherally by immune cells. Additionally, there are indications that cortisol is not only sufficient, but necessary, for the suppression of GnRH and gonadotropins in response to stress (Breen K M, Karsch F J. Front Neuroendocrin 2006; 27:233-45).

Females are more susceptible than males to GnRH and gonadotropin increases, which are also more profound, due to the menopausal transition, postpartum, and anti-oestrogen therapy. Thus, the findings may explain why females are not only more susceptible to RA, but also have more severe disease than males.

The advantage of a post hoc analyses is that they are based on predefined analyses for the entire AGRA population, and are clinically relevant. The results are considered reliable as they are in accordance with the results of the original AGRA trial. Both the original primary and key secondary endpoints were met despite performing analyses in a proof-of-concept trial with patients of longstanding disease, of whom 89% had previously failed disease-modifying antirheumatic drugs or 45% failed biologic therapy or failed both. Such baseline characteristics usually decrease beneficial responses to therapy (Andersson J J, et al., Arthritis Rheum 2000; 43:22-9). There was a trend towards slightly higher disease activity in controls (e.g. DAS28-CRP 5.2 vs. 5.0); although CRP was slightly lower in controls. It is not likely that this has substantially influenced results as all analyses are baseline-adjusted and there were no significant differences in any outcome measures at baseline. Furthermore, one could speculate that a greater reduction in disease activity would be more easily apparent in patients with higher disease activity (Andersson J J, et al., Arthritis Rheum 2000; 43:22-9). Inclusion criteria required that any patients on concomitant therapy had to be on long-term stable doses prior to study start. A varied concomitant DMARD background allowed the possibility of drug interactions that could confound the results. It is contemplated that it is unlikely that the results are confounded by this because baseline concomitant therapy was not significantly different between groups. The results indicate that GnRH, and/or gonadotropins are important in RA disease perpetuation.

TABLE 4

|  | All<br>N = 48 | High<br>Gonadotropins<br>N = 27 | Placebo<br>All<br>N = 51 | Placebo<br>High<br>Gonadotropins<br>N = 26 |
|---|---|---|---|---|
| DEMOGRAPHICS | | | | |
| Age, years | 54.9 ± 11.4 | 58.9 ± 8.3 | 55.0 ± 11.7 | 59.8 ± 8.8 |
| Female—no. (%) | 35 (73) | 26 (96) | 36 (71) | 26 (100) |
| Disease duration, years | 11.5 ± 10.6 | 12.9 ± 11.6 | 12.0 ± 12.9 | 15.6 ± 15.5 |
| Anti-CCP† antibody positive—no. (%) | 28 (58) | 15 (56) | 35 (69) | 15 (58) |
| Current smoker—no. (%) | 13 (27) | 14 (52) | 20 (39) | 12 (46) |
| CLINICAL AND LABORATORY MEASURES | | | | |
| DAS28-CRP‡ | 5.0 ± 1.0 | 5.0 ± 1.0 | 5.2 ± 1.0 | 5.2 ± 0.9 |
| LH§ (IU/L) | 20.4 ± 16.3 | 32.0 ± 12.4 | 19.6 ± 16.3 | 34.2 ± 9.8 |
| FSH¶ (IU/L) | 36.9 ± 30.0 | 59.5 ± 19.5 | 32.9 ± 31.1 | 60.4 ± 19.8 |
| C-reactive protein (mg/L) | 18.9 ± 24.5 | 23.0 ± 31.3 | 17.3 ± 22.5 | 20.6 ± 26.6 |
| ESRl (mm/h) | 22.0 ± 18.3 | 21.8 ± 20.2 | 25.8 ± 27.0 | 29.7 ± 30.4 |
| Cortisol (umol/L) | 392 ± 151 | 404 ± 158 | 401 ± 200 | 410 ± 213 |
| CURRENT MEDICATION | | | | |
| None—no. (%) | 11 (23) | 8 (30) | 12 (24) | 4 (15) |
| Stable NSAIDs**—no. (%) | 9 (19) | 5 (19) | 14 (27) | 6 (23) |
| Stable prednisolone ≤ 7.5 mg —no. (%) | 24 (50) | 13 (48) | 22 (43) | 12 (46) |
| Stable DMARDs††—no. (%) | 19 (40) | 9 (33) | 27 (53) | 15 (57) |
| MTX | 16 (33) | 8 (30) | 17 (33) | 10 (38) |
| LEF | 2 (4) | 0 | 2 (4) | 2 (8) |
| SSZ | 0 | 0 | 1 (2) | 0 |
| HCQ | 1 (2) | 1 (4) | 2 (4) | 2 (8) |
| MTX + SLZ | 0 | 0 | 3 (6) | 1 (4) |
| MTX, SSZ + HCQ | 0 | 0 | 2 (4) | 0 |
| PREVIOUS FAILURE TO DMARDS OR BIOLOGIC THERAPY‡‡ | | | | |
| Previous failure with any number of DMARDs—no. (%) | 40 (83) | 24 (89) | 45 (88) | 24 (92) |
| 1 previous DMARD | 13 (27) | 8 (30) | 13 (25) | 7 (27) |
| 2 previous DMARDs | 10 (21) | 6 (22) | 9 (18) | 4 (15) |
| ≥3 previous DMARDs | 17 (35) | 10 (37) | 23 (45) | 13 (50) |
| Previous failure with any number of biologics—no. (%) | 21 (44) | 12 (44) | 23 (45) | 11 (42) |
| 1 previous biologic | 9 (19) | 6 (22) | 9 (18) | 4 (15) |

TABLE 4-continued

|  | All<br>N = 48 | High<br>Gonadotropins<br>N = 27 | Placebo<br>All<br>N = 51 | Placebo<br>High<br>Gonadotropins<br>N = 26 |
|---|---|---|---|---|
| 2 previous biologics | 6 (13) | 2 (7) | 3 (6) | 2 (8) |
| ≥3 previous biologics | 6 (13) | 4 (15) | 11(22) | 5 (19) |

*Plus-minus values are means ± SD. There were no significant differences between groups in baseline characteristics, except for age and sex.
†CCP denotes Cyclic Citrullinated Peptide.
‡DAS28-CRP Disease Activity Score for 28-joint counts based on C-reactive protein (in which scores range from 2 to 9, with higher scores indicating more disease activity).
§LH denotes Luteinizing Hormone.
¶FSH denotes Follicle-Stimulating Hormone, Based on detectable FSH values <256 IU/L; N = 48 (cetrorelix), N = 50 (placebo).
∥ESR denotes Erythrocyte Sedimentation Rate.
**NSAIDs denotes Nonsteroidal Anti-Inflammatory Drugs.
††DMARDs denotes Disease-Modifying Anti-Rheumatic Drugs; MTX Methotrexate; SSZ Sulfasalazine; HCQ Hydroxychloroquine; and LEF Leflunomide.
‡‡Previous failure includes inefficacy or intolerability.

TABLE 5

Cytokine levels at baseline and final visit

| Cytokine (log pg/mL) | Baseline Day 1† | Final Day 15 | Change from baseline by day 15 | Baseline-Adjusted Between-Group Difference, 95% CI |
|---|---|---|---|---|
| PRO-INFLAMMATORY CYTOKINES | | | | |
| TNF-α§ Cetrorelix N = 27 | 0.46 ± 2.3 | 0.01 ± 2.1 | −0.45 | 0.49‡ |
| TNF-α Placebo N = 26 | 0.97 ± 3.0 | 0.99 ± 3.1 | +0.02 | (0.01, 0.96) |
| IL¶-1β Cetrorelix N = 27 | −1.48 ± 1.5 | −1.68 ± 1.4 | −0.20 | 0.30‡ |
| IL-1β Placebo N = 26 | −1.21 ± 2.4 | −1.11 ± 2.4 | +0.10 | (0.02, 0.59) |
| IL-2 Cetrorelix N = 27 | −2.97 ± 3.2 | −3.39 ± 2.9 | −0.42 | 0.51 |
| IL-2 Placebo N = 26 | −2.32 ± 3.7 | −2.29 ± 3.7 | +0.02 | (−1.09, 0.08) |
| ANTI-INFLAMMATORY CYTOKINE | | | | |
| IL-10 Cetrorelix N = 27 | 0.33 ± 2.1 | −0.31 ± 2.1 | −0.40 | 0.59‡ |
| IL-10 Placebo N = 26 | 0.16 ± 2.5 | 0.29 ± 2.5 | +0.13 | (0.10, 1.08) |

*Plus-minus values are means ± SD; Intention-to-treat analyses of cytokine levels between high-gonadotropin groups.
†No significant differences at baseline between groups in any cytokine.
‡P < 0.05.
§TNF-α denotes tumor necrosis factor-α.
¶IL denotes interleukin.

TABLE 6

Adverse events

| Event* | Cetrorelix, N = 27 | Placebo, N = 26 |
|---|---|---|
| Headache—no. % | 2 (7.4) | 3 (11.5) |
| Injection site discomfort—no. % | 2 (7.4) | 0 |
| Nausea—no. % | 0 | 2 (7.7) |

*There were no significant between-group differences.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention that are obvious to those skilled in molecular biology, in vitro fertilization, development, or related fields are intended to be within the scope of the following claims.

I claim:

1. A method of treating rheumatoid arthritis, comprising:
   a) identifying subjects that have increased levels of Gonadotropin Releasing Hormone (GnRH) or gonadotropins relative to a reference level, wherein said increased levels of GnRH or gonadotropins are Luteinizing Hormone (LH)>15 IU/L and/or Follicle Stimulating Hormone (FSH)>16.7 IU/L; and
   b) administering a GnRH antagonist to said subjects, wherein said GnRH antagonist is selected from the group consisting of cetrorelix, ganirelix, and degarelix.

2. The method of claim 1, wherein said increased levels of GnRH or gonadotropins are LH>17.3 IU/L and/or FSH>34.6 IU/L.

3. The method of claim 1, wherein said identifying comprises performing a quantitative diagnostic assay.

4. The method of claim 1, wherein said subject is a woman.

5. The method of claim 4, wherein said subject is a post-menopausal woman.

6. The method of claim 1, further comprising the step of administering an additional treatment for rheumatoid arthritis in combination with said GnRH antagonist.

7. A method of treating rheumatoid arthritis, comprising:
   a) identifying subjects that exhibit at least one criteria selected from the group consisting of negative for anti-cyclic citrullinated peptide (CCP) antibodies; non-responders to anti-TNF therapy or disease-modifying anti-rheumatic drugs (DMARDs); and not taking concomitant therapy; and
   b) administering a GnRH antagonist to the subjects, wherein said GnRH antagonist is selected from the group consisting of cetrorelix, ganirelix, and degarelix.

* * * * *